United States Patent [19]

Umezu et al.

[11] 4,386,502
[45] Jun. 7, 1983

[54] HUMIDITY-MEASURING DEVICE FOR USE WITH AN AIR CONDITIONER

[75] Inventors: Kenji Umezu; Kazuhiro Takazawa, both of Shizuoka; Toshiaki Hitosugi, Numazu; Eiji Kuwahara, Fuji, all of Japan

[73] Assignee: Tokyo Shibaura Denki Kabushiki Kaisha, Kawasaki, Japan

[21] Appl. No.: 280,353

[22] Filed: Jul. 6, 1981

[30] Foreign Application Priority Data

Jul. 8, 1980 [JP] Japan .................... 55-93135

[51] Int. Cl.³ .................. G01K 13/00; F25D 17/04
[52] U.S. Cl. .................. 62/129; 62/176 E; 62/180; 236/44 R
[58] Field of Search ............ 62/176 F, 176 R, 209, 62/126, 129, 180; 236/44 R; 73/338

[56] References Cited

U.S. PATENT DOCUMENTS 4,129,250 12/1978 Chaikin et al. .............. 73/338 X

FOREIGN PATENT DOCUMENTS 48-5310 2/1973 Japan .
54-129738 10/1979 Japan .
54-146447 11/1979 Japan ................ 62/176 E
829681 3/1956 United Kingdom .

Primary Examiner—William E. Wayner
Attorney, Agent, or Firm—Cushman, Darby & Cushman

[57] ABSTRACT

A humidity-measuring device used with an air conditioner provided with an interior heat exchanger and refrigerant pipe which comprises:

a first sensor which is provided at an inlet of the interior heat exchanger and produces a first output signal denoting a temperature of air streams drawn into the interior heat exchanger;

a heat conductor positioned in a state extending to the inlet at one end of that portion of the refrigerant pipe, through which the refrigerant flows with a low pressure;

a second sensor which is disposed in that portion of the heat conductor which faces the inlet and produces a second output signal; and a system controller which is provided with a memory for storing data on the air humidity corresponding to the first and second output signals, and measures the humidity of the sucked air from the data stored in the memory in accordance with the first and second output signals from the first and second sensors.

6 Claims, 8 Drawing Figures

HUMIDITY-MEASURING DEVICE FOR USE WITH AN AIR CONDITIONER

This invention relates to humidity-measuring device for use with an air conditioner which measures the humidity of air drawn into an interior heat exchanger.

With an air conditioner, adjustment of the humidity of air drawn thereinto is regarded as one of the important factors to assure a suitable interior air-conditioned state. A known process of measuring the humidity of air sucked into an interior heat exchanger (hereinafter referred to as "sucked air") comprises measuring the temperature of the sucked air, the temperature of a refrigerant supplied to the interior heat exchanger and the temperature of air blown out of the interior heat exchanger (hereinafter referred to as "discharged air") and determining the humidity of the sucked air from these measured data. Hitherto, the refrigerant temperature has been measured in a prescribed section of an interior heat exchanger. However, the temperature of a refrigerant widely varies throughout the interior heat exchanger, for example, with the operating condition of the interior heat exchanger and a sealed quantity of the refrigerant. In other words, the refrigerant temperature varies with the points of measurement in the interior heat exchanger. The conventional refrigerant temperature-measuring process gives erroneous data. Hitherto, therefore, the humidity of the sucked air has been determined with low precision due to such erroneous data being applied as one of the factors of measurement.

Another known process of measuring the humidity of the sucked air comprises measuring the temperature of the sucked air while the sucked air is contacted by drain water from the interior heat exchanger, and applying the measured air temperature in determining the humidity of the sucked air. However, the latter conventional air humidity-measuring process has the drawbacks that an appreciably long waiting time is involved, until a sufficient amount of drain water is collected in a receptacle for measurement of the temperature of the sucked air, and moreover difficulties are raised with respect to the contamination and decomposition of said drain water receptacle.

This invention has been accomplished in view of the above-mentioned circumstances, and is intended to provide an air humidity-measuring device for use with air conditioner which can determine the humidity of the sucked air with high precision without applying drain water from an interior heat exchanger.

To attain the above-mentioned object, this invention provides an air humidity-measuring device for use with an air conditioner (including an interior heat exchanger and a refrigerant pipe), which comprises:

first sensor means provided at an entrance of the interior heat exchanger to produce a first output signal indicating a temperature $T_e$ of air to be drawn into the interior heat exchanger;

heat-conducting means which is positioned at one end of that portion of a pipe through which a refrigerant flows with a low pressure, and extends to the entrance of the interior heat exchanger;

second sensor means provided in that end portion of the heat-conducting means which faces the entrance of the interior heat exchanger to send forth a second output signal showing a temperature $T_f$ of the end portion of the heat conductor; and means which measures the humidity of air to be drawn into the interior heat exchanger, and is provided with a memory for storing data or said humidity corresponding to said temperatures $T_e$, $T_f$, said measurement of air humidity being carried out from data previously stored in the memory in accordance with the first and second output signals from the first and second sensor means.

This invention can be more fully understood from the following detailed description when taken in conjunction with the accompanying drawings, in which.

Figure 1:
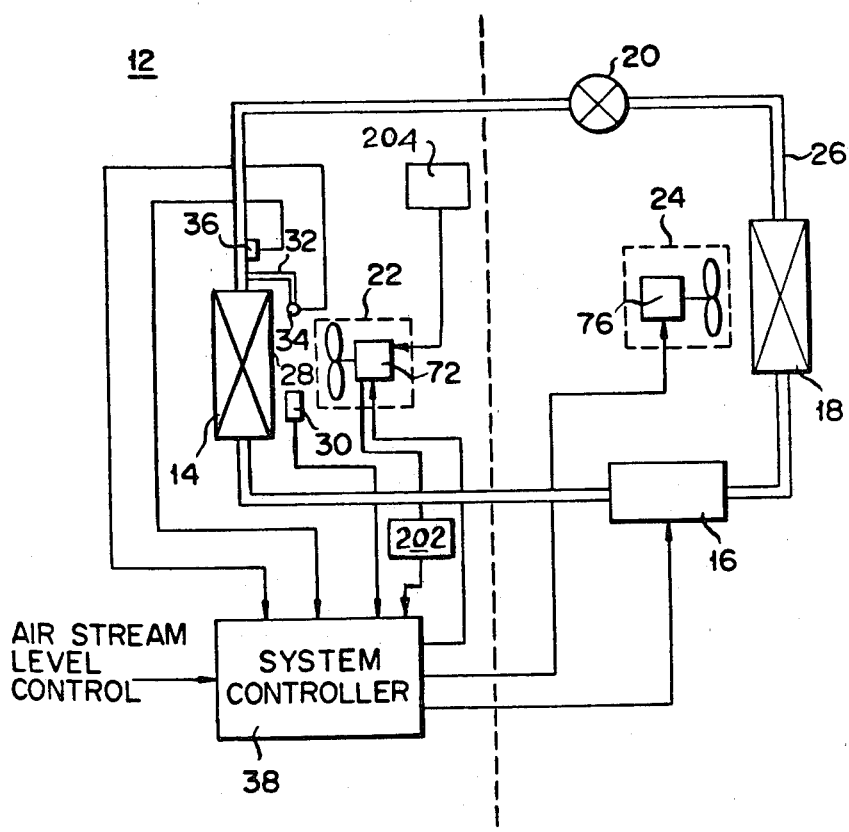
FIG. 1 shows a schematic arrangement of an air humidity-measuring device embodying this invention assembled with an air conditioner.
Figure 4:
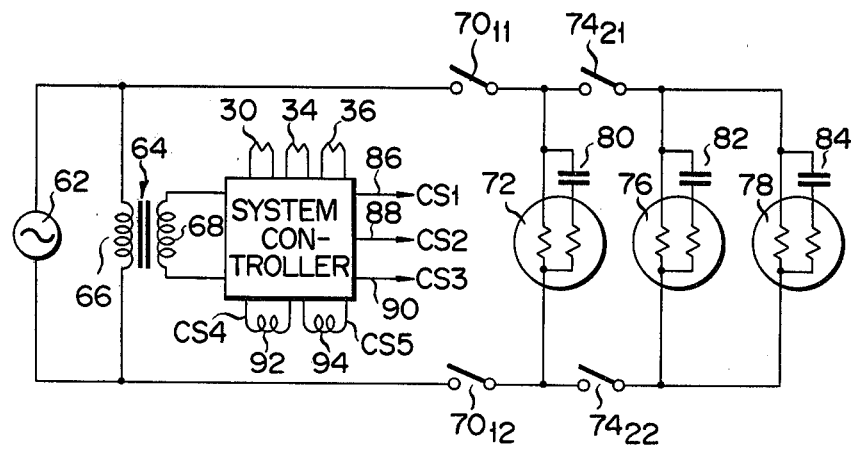
Figure 5:
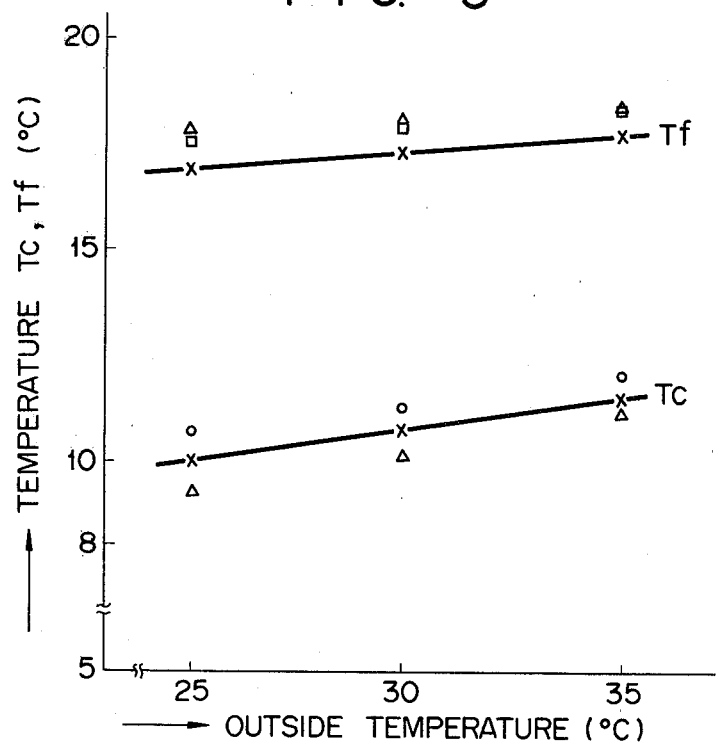
Figure 6:
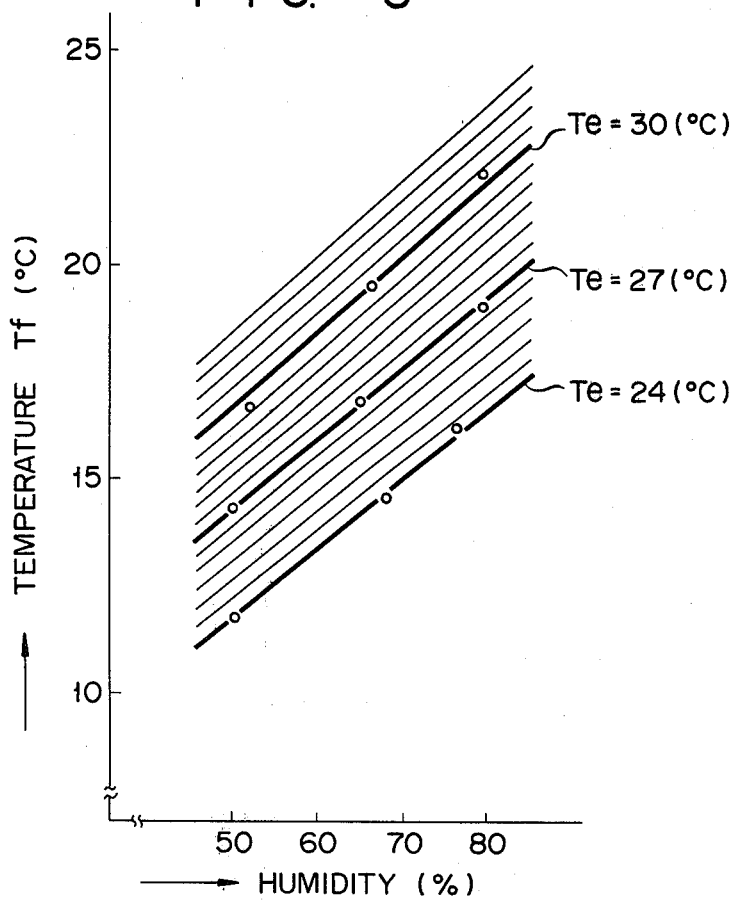
Figure 7:
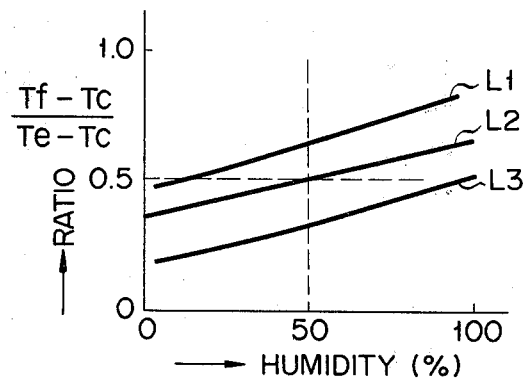
Figure 8:
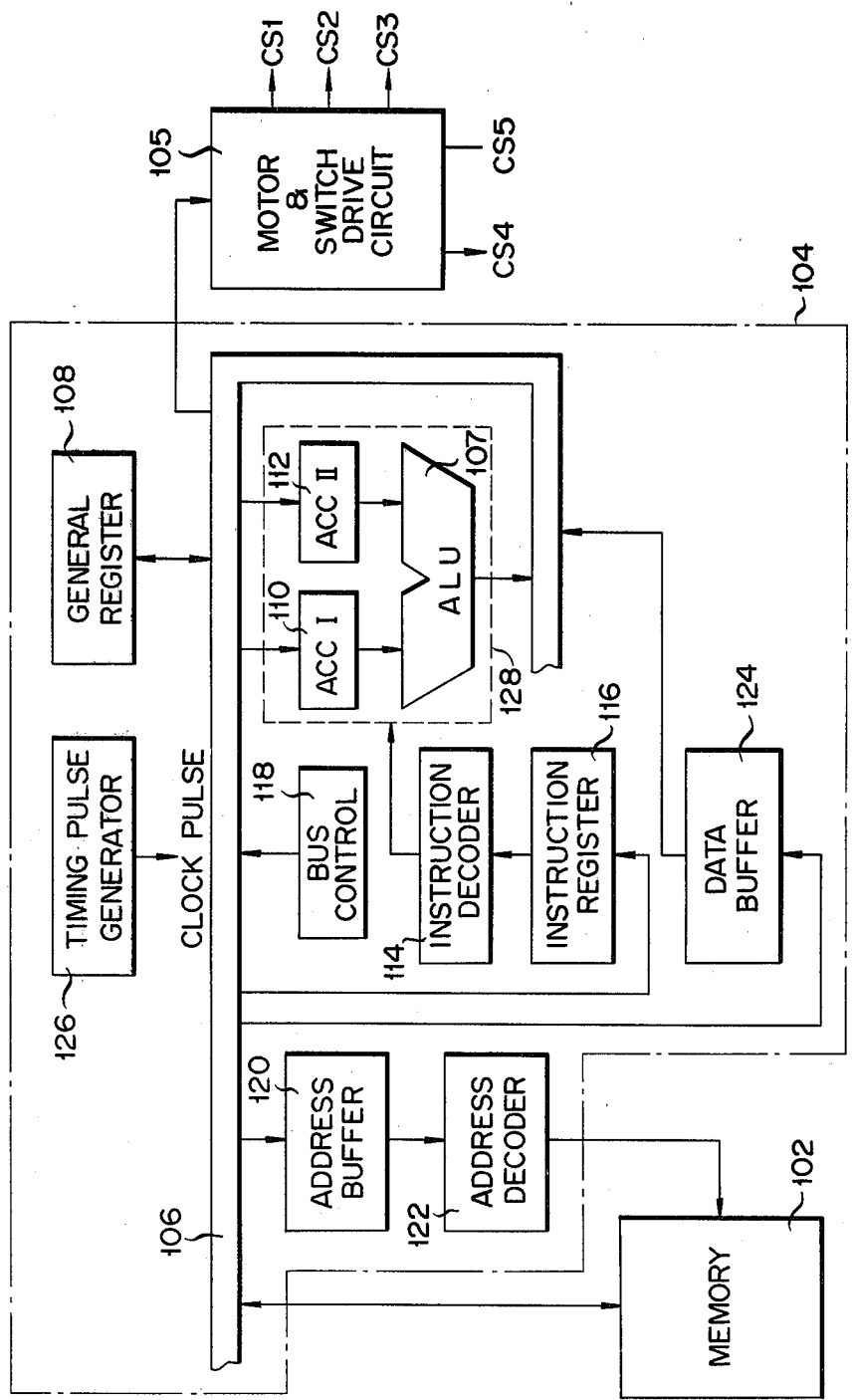

FIG. 4 indicates an arrangement of an electric circuit used with the air humidity-measuring device of FIG. 1;

FIG. 5 is a curve diagram showing relationship between open air temperature and the temperatures of sucked air measured by two sensors provided in the room;

FIG. 6 is a curve diagram indicating relationship between the humidity of sucked air and the air temperature measured by the two indoor sensors; and FIG. 7 is a curve diagram setting forth the ratio which the humidity of sucked air bears to the temperatures of, indoor air measured at a plurality of indoor spots; and FIG. 8 shows an arrangement of a system controller assembled with the humidity-measuring device of FIG. 1;

Description is now given with reference to the accompanying drawings of an air humidity-measuring device embodying this invention.

FIG. 1 shows the air humidity-measuring device of the invention used with an air conditioner. The air conditioner consists of a cooling-heating system comprising an interior heat exchanger 14 set in the room whose air condition is to be determined; and outdoor members such as a compressor 16, exterior heat exchanger 18 and expansion means 20 such as a capillary tube. The compressor 16 compresses a refrigerant delivered from the interior heat exchanger 14. The exterior heat exchanger 18 condenses a refrigerant of high temperature and high pressure sent forth from the compressor 16. The expansion means 200 expands a refrigerant flowing from the exterior heat exchanger 18 to reduce the temperature and pressure of said refrigerant, and supplies the refrigerant thus treated to the interior heat exchanger 14.

The interior heat exchanger 14 and exterior heat exchanger 18 are respectively provided with blowers 22, 24. The interior heat exchanger 14, compressor 16, exterior heat exchanger 18 and expansion means 20 are connected in the order mentioned by a refrigerant pipe 26 to form a refrigeration cycle.

The components of the air humidity-measuring device of this invention are fitted to the above-mentioned air conditioner in the undermentioned manner.

An air inlet 28 of the interior heat exchanger 14 is fitted with a sensor 30 formed of, for example, a thermistor to measure the temperature of the sucked air. A refrigerant flow with pressure through that portion of the refrigerant pipe 26 which extends at least between the expansion means 20 and the proximity of the interior heat exchanger 14. That portion of the refrigerant pipe 26 which faces and proximity of the interior heat exchanger 14 is fitted with a heat conductor 32 which extends to the air inlet 28. That portion of the heat conductor 32 which is positioned near the air inlet 28 is provided with a temperature sensor 34 formed of, for example, a thermistor. That portion of the refrigerant pipe 26 which lies near the interior heat exchanger 14 is provided with a temperature sensor 36 formed of, for example, a thermistor to measure the temperature of the above-mentioned portion of the refrigerant pipe 26. The air-humidity measuring device of this invention is further provided with a system controller 38 formed of a microcomputer (not shown in FIG. 1) comprising a memory. The system controller 38 measures the humidity of the sucked air by a prescribed operation in accordance with output temperature signals from the temperature sensors 30, 34, 36. The system controller 38 further supplies control signals to a fan motor 72 of the interior blower 22, a fan motor 76 of the exterior blower 24 and a motor 78 (FIG. 4) of the compressor 16 to control the running speed of these motors, thereby maintaining the humidity of the indoor atmosphere in a suitable condition.

The temperature sensor 36 should preferably be positioned, as shown in FIG. 1, near that portion of the refrigerant pipe 26 which is fitted with the heat conductor 32, or the return bend of that portion of the refrigerant pipe 26 which extends through the interior heat exchanger 14.

Figure 2:
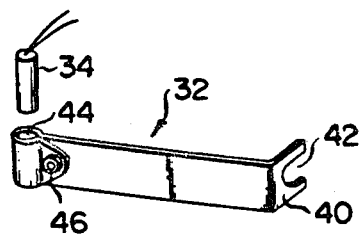
FIG. 2 is an oblique view of a heat-conducting member used with the air humidity-measuring device of FIG. 2.
Figure 3:
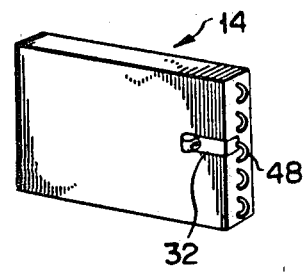
FIG. 3 shows the heat-conducting member of FIG. 2 fitted to a return bend portion of a refrigerant pipe extending through an interior heat exchanger.

The heat conductor 32 is preferred to be a fin having an L-shaped cross section as seen from FIG. 2, and further be made of the same material as that of the refrigerant pipe 26 to facilitate solding. Namely, the heat conductor 32 is desired to be formed of copper or aluminium, where the regrigerant pipe 26 is prepared from copper or aluminium. A semicircular notch 42 complementary to the shape of the outer peripheral wall of the refrigerant pipe 26 is cut in that end portion 40 of the heat conductor 32 which is to be fitted to the refrigerant pipe 26 in order to assure the secure attachment of the heat-conductor 32 to the refrigerant pipe 26. The opposite end portion of the heat conductor 32 is bent in the circular form to provide a cylindrical section 44. A temperature sensor 34 is inserted into the cylindrical section 44. The foremost tip portion of the aforesaid opposite side of the heat conductor 32 in which the cylindrical section 44 is formed is tightly fitted to the body of said heat conductor 32 by a screw 46, thereby causing the temperature sensor 34 to be tightly held in said cylindrical section 44. FIG. 2 shows the temperature sensor 34 removed from the cylindrical section 44. FIG. 3 illustrates the heat conductor 32 of FIG. 2 fitted to one of the return bend sections 48 of the refrigerant pipe 26 extending through the interior heat exchanger 14.

FIG. 4 shows the arrangement of an electric circuit used with the air conditioner of FIG. 1. Reference numeral 62 denotes a commercial power source. A primary winding 66 of a transformer 64 is connected between both terminals of said commercial power source 62. A secondary winding 68 of the transformer 64 is connected to a drive terminal of the system controller 38. A drive motor 72 of the interior blower 22 is connected between both terminals of the commercial power source 62 through switches $70_{11}$, $70_{12}$. Connected in parallel to the motor 72 through switches $74_{21}$, $74_{22}$ are a drive motor 76 of the exterior blower 24 and a drive motor 78 of the compressor 16 both connected in parallel. Phase-advancing capacitors 80, 82, 84 are respectively connected to the motors 72, 76, 78.

With the electric circuit arranged as described above, the system controller 38 carries out a prescribed operation upon receipt of output temperature signals from the aforesaid three temperature sensors 30, 34, 36 to measure the humidity of the sucked air. The system controller 38 sends forth control signals $CS_1$, $CS_2$, $CS_3$ respectively to the motors 72, 76, 78 through the corresponding control lines 86, 88, 90 to set the running speed of the motors 72, 76, 78 at an optimum level. Between the motor 72 and the system controller 38 is a speed detector 202 provided for detecting the running speed of the sucked air. Of course, before sending the control signals $CS_1$, $CS_2$, $CS_3$, the system controller 38 receives a detection signal from the speed detector 202. The running speed of motors 72, 76, 78 is controlled by either the intermittent drive of any of said motors or varying the running speed thereof continuously or stepwise.

Reference numerals 92, 94 are electromagnetic coils for controlling the operation of the corresponding groups of switches $70_{11}$–$70_{12}$ and $74_{21}$–$74_{22}$. The switches $70_{11}$, $70_{12}$ are actuated by the electromagnetic coil 92. The switches $74_{21}$, $74_{22}$ are operated by the electromagnetic coil 94. The electromagnetic coils 92, 94 are energized by output control signals $SC_4$, $SC_5$ from the system controller 38. The operation of the motors 72, 76, 78 and switches $70_{11}$, $70_{12}$, $74_{21}$, $74_{22}$ is already known to the prior art, description of the electric circuit of FIG. 4 being given to the above extent.

The following facts have been experimentally recognized with the air humidity measuring device arranged as described above. Namely, the humidity of the sucked air can be measured from relationship between a temperature $T_f$ of the end of the heat conductor 32 detected by the sensor 34 fitted to the end of the heat conductor 32 and a temperature $T_e$ of the sucked air detected by the sensor 30. Further, the humidity of the sucked air can also be determined from relationship between a temperature $T_c$ of the lower pressure side of the refrigerant pipe 26 detected by the sensor 36, and a temperature $T_e$ of the sucked air measured by the sensor 30. Where, however, atmospheric temperature varies, then changes arise in the refrigerant pipe temperature $T_c$ determined by the sensor 36 and the temperature $T_f$ of that end portion of the heat conductor 32 (which extends to the inlet 28 of the interior heat exchanger 14) measured by the sensor 34, resulting in the occurrence of errors in the measured humidity of even the same sucked air.

FIG. 5 shows that smaller changes appear in the temperature $T_f$ of the end portion of the heat conductor 32 than in the detected temperature $T_c$ related to the humidity of the sucked air. In FIG. 5, the outside temperature (degrees C.) is shown on the abscissa, and the temperatures $T_c$, $T_f$ are indicated on the ordinate. The reason for the occurrence of the above-mentioned fact is supposed to be that the sensor 36 directly measures the temperature $T_c$ of the refrigerant pipe 26, and said temperature $T_c$ is immediately affected by changes in the atmospheric temperature, where as the sensor 34 is connected to the refrigerant pipe 26 through the heat conductor 32, which acts as a sort of heat-absorbing member with respect to changes in the atmospheric temperature, and consequently the temperature $T_f$ measured by the sensor 34 is not directly affected by changes in the atmospheric temperature. Moisture contained in the sucked air settle on the outer peripheral wall of the heat conductor 32 in the form of water droplets. Therefore, the temperature of the heat conductor 32 is naturally affected by these water droplets. Therefore, the temperature $T_f$ of the end portion of the heat conductor 32 measured by the sensor 34 is supposed to involve a factor already affected to some extent by the moisture or humidity of the sucked air.

The humidity of the sucked air can be determined with high precision once the interrelationship between the temperature $T_f$ of the end portion of the heat conductor 32 measured by the sensor 34 and the temperature $T_e$ of the sucked air measured by the sensor 30 have been experimentally determined. It has also been disclosed that where air streams are brought into the interior heat exchanger 14 at a variable speed, then the humidity of the sucked air can be detected with higher precision by adding the running speed of air streams to the aforementioned relationship between both temperature $T_e$, $T_f$. The running speed of air streams may be manually selected or set at an optimum level by the system controller 38. When it is attempted to manually select the running speed, the air humidity-measuring device of FIG. 1 should further include a speed setting circuit 204 which is manually operated to produce a control signal for controlling the running speed of the interior drive motor 72, so that the running speed of the air stream sent forth into the interior heat exchanger 14 may be set at a desired predetermined level.

FIG. 6 graphically shows relationship between the humidity (%) of the sucked air determined with the temperature $T_e$ (°C.) measured by the sensor 30 used as a parameter and the temperature $T_f$ (°C.) detected by the sensor 34. The humidity (%) of the sucked air is shown on the abscissa, and the temperature $T_f$ (°C.) detected by the sensor 34 is indicated on the ordinate. FIG. 6 is a curve diagram denoting the case where air streams were made to run at a high speed. For briefness of representation, data is not shown with respect to the slow running speed of air streams. Where air streams are made to flow at lower speed, then the curves given in FIG. 6 maintain their constant shape but are displaced towards the abscissa in the form exactly as indicated. Experimentally obtained broad curves of FIG. 6 respectively represent the temperatures $T_e$ (°C.) of 24, 27, 30. Other narrow assumed curves are indicated by dividing an area between the adjacent experimental broad curves at the rate of 0.5° C. The relationship of FIG. 6 is stored in the memory of the system controller 38 in the graphical or functional form. In this case, data on the temperatures $T_e$, $T_f$ specify addresses, and data on the humidity of the sucked air are stored in said addresses.

Description is now given of the operation of an air humidity-measuring device embodying this invention when used with an air conditioner. For a certain length of time, after the start of the air conditioner, a refrigerant flows at an irregular rate and in an unstable form. Therefore, the temperature $T_c$ (measured by the sensor 36) of that portion of the refrigerant pipe 26 which extends between the expansion means 20 and the proximity of the interior heat exchanger 14 changes with time. The refrigerant generally attains a stable condition in 5 to 20 minutes. During the period in which the air conditioner reaches a stable state after its start, the temperature $T_c$ measured by the sensor 36 changes with time. Where, therefore, it is attempted to apply the temperature $T_c$ as data for measurement of the humidity of the sucked air, then errors arise in the humidity of the sucked air thus measured.

With the foregoing embodiment, therefore, data obtained only after the air conditioner has indicated a stable operation is used to determine the humidity of the sucked air. The above-mentioned control is effected under control of the system controller 38.

When the air conditioner has attained a stable condition, the system controller 38 carries out a prescribed operation in accordance with the temperature $T_e$ detected by the sensor 30, temperature $T_f$ detected by the sensor 34, and the prescribed running rate of air streams, and by applying the aforementioned relationship stored in the memory graphical or functional form, thereby determining the humidity of the sucked air.

The humidity of the sucked air is determined in the following manner. The detected temperatures $T_e$, $T_f$ are used to specify the addresses of the memory. Determination is made of the humidity of the sucked air corresponding to the temperatures $T_e$, $T_f$ stored in the specified addresses.

In accordance with the detected humidity of the sucked air, the system controller 38 sends forth control signals $CS_1$, $CS_2$, $CS_3$ for regulating the running speed of the motors 72, 76, 78 to the motors 72, 76 of the blowers 14, 18 and the motor 78 of the compressor 16 through the corresponding control lines 86, 88, 90. The motors 72, 76, 78 have their running speed controlled by said control signals $CS_1$, $CS_2$, $CS_3$. These control signals defined from the humidity of the sucked air detected with few errors carry out control with high precision, enabling the motors 72, 76, 78 to be driven in an optimum condition, and consequently the indoor atmospheric condition to be properly maintained.

The groups of switches $70_{11}$–$70_{12}$ and $74_{21}$–$74_{22}$ are respectively actuated by the coils 92, 94 energized by output control signals $CS_4$, $CS_5$ from the system controller 38. Where the switches $70_{11}$, $70_{12}$ are rendered nonconducting, then power supply to the motors 72, 76, 78 is cut. The air conditioner ceases to be operated due to the stoppage of the run of said motors. Where the switches $70_{11}$, $70_{12}$ are rendered conducting, and the switches $74_{21}$, $74_{22}$ remain inoperative, then the motor 72 alone is driven. In such case, indoor cooling is not effected, but only ventilation is carried out.

The sucked air humidity-measuring device of this invention arranged as described above has the advantages that the temperature of the sucked air is detected with high precision; since the moisture of the sucked air is deposited on the heat conductor 32 in the form of water droplets, the measurement of the temperature of the sucked air involves a factor affected by said water droplets, thereby enabling the humidity of the sucked air to be determined with few errors; the temperature of the sucked air measured during the period which extends from a point of time at which an air conditioner is started to a point of time at which said air conditioner reaches a stable condition is prevented from being adopted as data for determining the humidity of the sucked air, thereby enabling the humidity of the sucked air to be determined with few errors; since it is unnecessary to collect water drained from the interior heat exchanger, it is possible to eliminate a relatively long waiting time which might otherwise be required until a sufficient amount of water is collected in a water receptacle for the commencement of the determination of the humidity of the sucked air; and difficulties are prevented from being raised by for example, the contamination or decomposition of the drain water receptacle.

Description is now given with reference to FIGS. 1 to 4 and FIG. 7 of an air humidity-measuring device according to a second embodiment of this invention.

The second embodiment is different from the first embodiment in that in the second embodiment, the humidity of the sucked air is determined, as later described, from the refrigerant pipe temperature $T_c$ measured by the sensor 36. The refrigerant pipe temperature $T_c$ is applied as a factor in the following equation for calculating the humidity of the sucked air in which $T_f(°C.)$ denotes the temperature of the sucked air detected by the sensor 34:

$$T_f = T_e - (T_e - T_c)\left(\cos H\sqrt{\frac{2H}{DK}}\ L\right)^{-1}$$

where:
$T_e$=sucked air temperature (°C.) detected by the sensor 30
$T_c$=refrigerant pipe temperature (°C.) detected by the sensor 36
H=thermal transfer rate (Kcal/m²h°C.) of heat transfer from the heat conductor 32 to the sucked air
k=thermal conductivity (Kcal/m²h°C.) through the heat conductor 32
D=thickness (mm) of the heat conductor 32
L=length (mm) of the heat conductor 32

In the above equation, the factors $T_c$ and H are taken to vary with the humidity of the sucked air. Where studies were made on the relationship between the humidity of the sucked air and the ratio of $(T_f-T_c)$ to $(T_e-T_c)$, then the relationships indicated by the curves of FIG. 7 were found to exist. The humidity (%) of the sucked air is shown on the abscissa, and the ratio of $(T_f-T_c)$ to $(T_e-T_c)$ is indicated on the ordinate. In FIG. 7, the characters $L_1$, $L_2$, $L_3$ respectively represent the high, medium and low rates of air streams sent forth by the blower 22 of the interior heat exchanger 14. The relationships given in FIG. 7 are stored in the memory of a microcomputer in the substantially same graphic or functional form as in the first embodiment.

Description is now given of an air humidity-measuring device according to the second embodiment of this invention applied to an air conditioner, in which the relationships of FIG. 7 are stored in the memory in the graphic or functional form as in the first embodiment. With the second embodiment, the refrigerant pipe temperature $T_c$ measured before stabilized is considered as inapplicable to the measurement of the humidity of the sucked air. In other words, the refrigerant pipe temperature $T_c$ measured only after stabilized is adopted as data applicable to the detection of the humidity of the sucked air.

Where the refrigerant pipe temperature $T_c$ gets stabilized, then the temperatures $T_e$, $T_f$, $T_c$ detected by the sensors 30, 34, 36 under the control of the system controller 38 are adopted as data for detection of the humidity of the sucked air. The system controller 38 calculates the value of the ratio of $(T_f-T_c)$ to $(T_e-T_c)$ from the relationship shown in FIG. 7 stored in the memory in the graphic or functional form by applying the calculated value of the above-mentioned ratio and the prescribed running speed of air streams sent forth from the blower. The operation following based on the detected humidity of the sucked air is the same as in the first embodiment, description thereof being omitted.

As in the first embodiment, the second embodiment offers not only the same advantages as in the first embodiment, but also the merit that the refrigerant pipe temperature $T_c$ detected by the sensor 36 is used as one of the factors to define the humidity of the sucked air, thereby enabling said humidity to be determined with higher precision than in the first embodiment.

Description is now given of the arrangement and operation of the system controller 38 shown in FIG. 1 with reference to FIG. 8 showing the arrangement of said system controller 38 assembled with the humidity-measuring device of FIG. 1.

The controller 38 comprises a memory 102, central processing unit (CPU) 104 and motor and switch drive circuit 105. The memory 102, CPU 104 and drive circuit 105 are connected together by means of a bus 106.

A relationship shown in FIG. 7 is stored in the memory 102 is the graphical or functional form. In addition, instructions for various forms of arithmetic operation are stored in the memory 102.

The CPU 104 comprises:
a general register 108 which temporarily stores data on the detected temperatures $T_e$, $T_f$, $T_c$ and also the result of an arithmetic operation carried out by the later described arithmetic logic unit (ALU) 107;

an accumulator I 110 which reads out data on the detected temperatures $T_f$, $T_c$ stored in the general register 108 to carry out an arithmetic operation of $(T_f-T_c)=T_1$;

an acumulator II 112 which reads out data on the detected temperatures $T_e$, $T_c$ stored in the general register 108 to carry out an arithmetic operation of $(T_e-T_c)=T_2$;

the arithmetic logic unit (ALU) 107 for carrying out an arithmetic operation of $(T_1/T_2)$ from the results of the arithmetic operations performed by the accumulators 110, 112 in accordance with the contents of an instruction issued from the later described instruction decoder 114;

an instruction register 116 for temporarily storing an instruction fetched from the memory 102;

the instruction decoder 114 for decoding the contents of an instruction read out of the instruction register 116;

a bus control 118 for controlling the transfer of data through a bus 106;

an address buffer 120 for fetching from the general register 108 the result of an arithmetic operation undertaken by the ALU 107 in the form of an address signal and temporarily storing said address signal;

an address decoder 122 for decoding an address signal fetched from the address buffer 120;

a data buffer 124 for temporarily storing data on air humidity fetched from the specified address of the memory 102 upon receipt of an address signal from the address decoder 122; and a timing pulse generator for issuing pulse signals to control the timing in which the constituent circuits of the CPU 104 are operated.

Description is now given of the manner in which levels of air humidity corresponding to the detected temperatures $T_e$, $T_f$, $T_c$ are determined in the controller 38 arranged as described above.

First, an instruction for the arithmetic operation of $(T_f-T_c)/(T_e-T_c)$ is fetched from the memory 102 to the instruction register 116 through the bus 106. An instruction fetched from the instruction register 116 is decoded by the instruction decoder 114.

Upon receipt of a decoded instruction from the instruction decoder 114, a logic circuit 128 formed of the accumulator I 110 and accumulator II 112 and ALU 107 carries out a logic operation of the detected temperatures $T_e$, $T_f$, $T_c$ in accordance with the contents of the decoded instruction. This logic operation is carried out as follows. Data on the temperatures $T_e$, $T_f$, $T_c$ detected by the corresponding sensors 30, 34, 36 are temporarily stored in the general register 108 through the bus 106. Data on the detected temperatures $T_f$, $T_c$ are fetched from the general register 108 to the accumulator I 110 under control of a timing signal issued from the timing pulse generator 126. Data on the detected temperatures $T_e$, $T_c$ are fetched from said general register 108 to the accumulator II 112 similarly under control of a timing signal. In accordance with the contents of a decoded instruction issued from the instruction decoder 114, the accumulator I 110 carries out an arithmetic operation of $(T_f - T_c) = T_1$, and the accumulator II 112 carries out an arithmetic operation of $(T_e - T_c) = T_2$. The results of arithmetic operations conducted by the accumulator I 110 and accumulator II 112 are supplied to the ALU 107, which in turn performs an arithmetic operation of $(T_1/T_2) = (T_f - T_c)/(T_e - T_c)$. The result of an arithmetic operation undertaken by the ALU 107 is temporarily stored in the general register 108 through the bus 106. The result of the arithmetic operation is fetched as an address signal from the general register 108 to the address buffer 120 through the bus 106. An address signal read out of the address buffer 120 is decoded by the address decoder. Any of the addresses of the memory 102 is specified by the decoded address signal. A relationship between the term $(T_f - T_c)/(T_e - T_c)$ and the corresponding level of air humidity is stored in the memory 102. Therefore, a level of air humidity corresponding to said term is read out of the specified address of the memory 102. Data on the air humidity is temporarily stored in the data buffer 124. Said data is supplied from the data buffer 124 to the motor-switch drive circuit 105 through the bus 106. The drive circuit 105 sends forth, the accordance with the contents of data on air humidity by the known process, control signals $CS_1$, $CS_2$, $CS_3$ and also control signals $CS_4$, $CS_5$ to control the operation of the switches $70_{11}$, $70_{12}$. The above-mentioned arrangement assures proper air conditioning.

As described above, this invention is characterized in that the sensor 30 for detecting the sucked air temperature is positioned near the inlet 28 of the interior heat exchanger 14; a fin-shaped heat conductor 32 extending to said inlet 28 is set on the peripheral wall of that portion of the refrigerant pipe 26 which lies near the interior heat exchanger 14; the temperature sensor 34 is fitted to that end of the heat conductor 32 which faces the inlet 28 of the interior heat exchanger 14.

Therefore, the present invention offers the advantages that the temperature of the sucked air is detected with high precision; since the moisture contained in the sucked air settles on the surface of heat conductor 32, the temperature of the sucked air is determined in the form already affected by said moisture, thereby reducing errors in the detected humidity of the sucked air; the temperature of the sucked air measured before the refrigerant pipe temperature gets stabilized after the start of the air conditioner is prevented from being applied to the practical determination of the humidity of the sucked air, thereby reducing errors in the detected humidity of the sucked air; drain water from the interior heat exchanger need not be collected, thereby eliminating a relatively long waiting time required until a sufficient amount of water is collected in the drain water receptacle for the commencement of the temperature and humidity of the sucked air; and difficulties are prevented from arising from the contamination and decomposition of the drain water receptacle. Since a sensor fitted to the end of the heat conductor extending to the refrigerant pipe also detects the temperature of the sucked air, it is possible to omit another sensor directly mounted on the peripheral wall of the refrigerant pipe, thereby simplifying the arrangement of the air humidity-measuring device of this invention and reducing its cost.

What we claim is:

1. A humidity-measuring device used with an air conditioner provided with an interior heat exchanger and refrigerant pipe which comprises:

first sensor means disposed at an inlet of the interior heat exchanger to produce a first output signal denoting a temperature $T_e$ of an air stream to be drawn into the interior heat exchanger;

heat-conducting means which is positioned at one end of that portion of the pipe through which a refrigerant flows with a low pressure, and extends to the entrance of the interior heat exchanger;

second sensor means fitted to that end portion of the heat conductor which faces the inlet of the interior heat exchanger to send forth a second output signal showing a temperature $T_f$ of said end portion of the heat conductor; and air humidity-measuring means which is provided with a memory for storing data on the humidity of the sucked air corresponding to the temperatures $T_e$, $T_f$, and determines said air humidity from the data stored in the memory in accordance with output signals from the first and second sensor means.

2. The humidity-measuring device according to claim 1, wherein third sensor means is further mounted on that portion of the refrigerant pipe through which a refrigerant flows with a low pressure and produces a third output signal denoting a temperature $T_c$ of the regrigerant pipe; and said air humidity-measuring means is provided with a memory for storing data on the temperatures $T_e$, $T_f$, $T_c$ and determines the humidity of the sucked air from the data stored in the memory in accordance with the first, second and third output signals from the first, second and third sensor means.

3. The humidity-measuring device according to claim 2, wherein the memory stores data on the relationship between the humidity of the sucked air and a ratio of $(T_f - T_c)$ to $(T_e - T_c)$; and the air humidity-measuring means measures the humidity of the sucked air from said relationship in accordance with the first, second and third output signals from the first, second and third sensor means.

4. The humidity-measuring device according to claim 1, wherein there is further provided means for detecting the running speed of air streams sent forth into the interior heat exchanger and producing a third output signal denoting said running speed of air streams; the memory stores data on air humidity corresponding to the temperatures $T_e$, $T_f$ and the running speed of air streams introduced into the interior heat exchanger; and the air humidity-measuring means determines the humidity of the sucked air from data stored in the memory in accordance with the first and second output signals from the first and second sensor means and the third output signal from the means for detecting the running speed of air streams blown into the interior heat exchanger.

5. The humidity-measuring device according to claim 2, wherein there is further provided means for detecting the running speed of air streams drawn into the interior heat exchanger and producing a fourth output signal denoting said running speed of air streams; the memory means stores data on the temperatures $T_e$, $T_f$, $T_c$ and the running speed of air streams carried into the interior heat exchanger; and the air humidity-measuring means determines the humidity of the sucked air from the data stored in the memory in accordance with the first, second and third output signals from the first, second and third sensor means and the fourth output signal from the air speed-detecting means.

6. The humidity-measuring device according to claim 1, wherein there is further provided means manually operable for setting the running speed of air streams sent forth into the interior heat exchanger at a desired level and producing a third output signal denoting said running speed of air streams; the memory stores data on air humidity corresponding to the temperatures $T_e$, $T_f$ and the running speed of air streams introduced into the interior heat exchanger; and the air humidity-measuring means determines the humidity of the sucked air from data stored in the memory in accordance with the first and second output signals from the first and second sensor means and the third output signal from the means for setting the running speed of air streams blown into the interior heat exchanger.

* * * * *